United States Patent [19]

Uchino et al.

[11] Patent Number: 5,310,918

[45] Date of Patent: May 10, 1994

[54] 1-ARYL-SUBSTITUTED AZOLE, NON-LINEAR OPTICAL MATERIAL AND NOVEL MOLECULAR CRYSTAL CONTAINING SAME AND METHOD AND MODULE FOR THE CONVERSION OF LIGHT WAVELENGTH USING SAME

[75] Inventors: Nobuhiko Uchino; Masaki Okazaki; Makoto Ishihara; Akinori Harada; Yoji Okazaki; Kazumi Kubo, all of Kanagawa, Japan

[73] Assignee: Fuji Photo Film Co., Ltd., Kanagawa, Japan

[21] Appl. No.: 700,285

[22] Filed: May 15, 1991

[30] Foreign Application Priority Data

May 16, 1990 [JP] Japan .................................. 2-125848
Jul. 20, 1990 [JP] Japan .................................. 2-192405
Sep. 21, 1990 [JP] Japan .................................. 2-253199

[51] Int. Cl.$^5$ .................. C07D 401/00; C07D 249/12; C07D 207/30
[52] U.S. Cl. ..................................... 546/276; 546/281; 548/265.8; 548/335.5; 548/373.1; 548/374.1; 548/561
[58] Field of Search ...................... 546/276; 548/373.1; 548/374.1

[56] References Cited

FOREIGN PATENT DOCUMENTS 144329 9/1988 Japan .

Primary Examiner—José G. Dees
Assistant Examiner—Keith MacMillan
Attorney, Agent, or Firm—Sughrue, Mion, Zinn, Macpeak & Seas

[57] ABSTRACT

Disclosed is a non-linear optical material represented by the following formula:

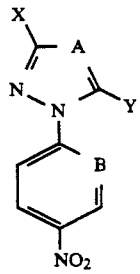

wherein X represents a methyl group or a hydrogen atom, with the proviso that when X is a methyl group, A represents a nitrogen atom, Y represents a methyl group and B represents a nitrogen atom; and when X is a hydrogen atom, A represents C—COOC$_2$H$_5$, Y represents a hydrogen atom and B represents C—CH$_3$.

In one embodiment, the non-linear optical material is represented by the following formula (I):

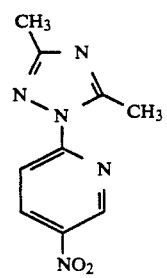

In another embodiment, the non-linear optical material is represented by the following formula (II):

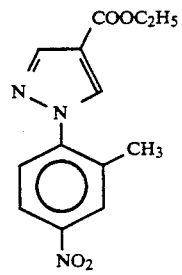

Also disclosed is an orthorhomic molecular crystal having a space group of Pna2$_1$ and constituted by molecules represented by the above formula (I).

2 Claims, 6 Drawing Sheets

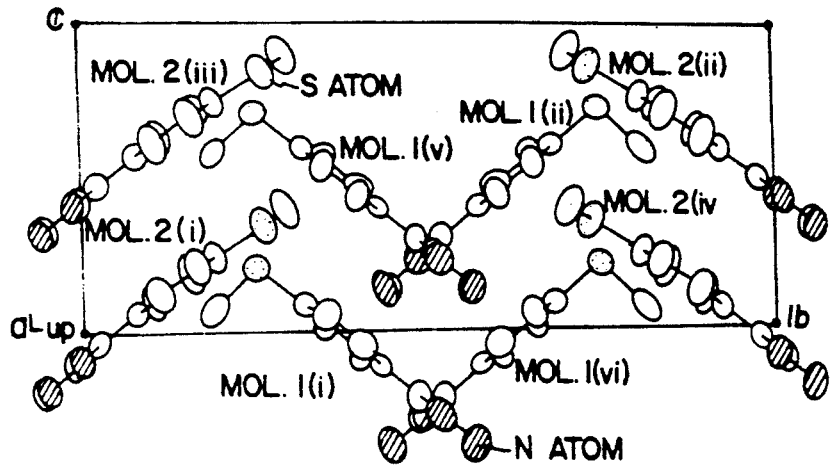
FIG. 3a
MOL. = MOLECULE
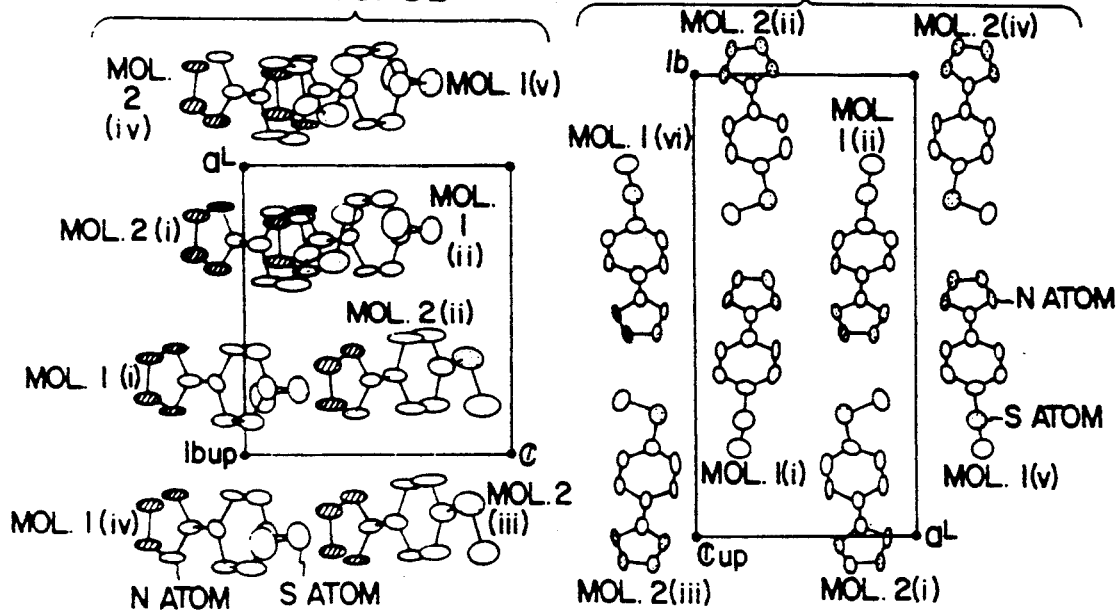
FIG. 3b
FIG. 3c

1-ARYL-SUBSTITUTED AZOLE, NON-LINEAR OPTICAL MATERIAL AND NOVEL MOLECULAR CRYSTAL CONTAINING SAME AND METHOD AND MODULE FOR THE CONVERSION OF LIGHT WAVELENGTH USING SAME

FIELD OF THE INVENTION

The present invention relates to a novel compound and molecular crystal useful as non-linear optical material. The present invention also relates to a method and module for the conversion of light wavelength using such a molecular crystal as non-linear optical material.

BACKGROUND OF THE INVENTION

In recent years, non-linear optical materials, i.e., materials having non-linearity between polarization and electric field developed when given a strong light field such as laser light have drawn public attention.

Such materials are generally known as non-linear optical materials and are described in detail in, for example, "Nonlinear Optical Properties of Organic and Polymeric Material", ACS SYMPOSIUM SERIES 233, edited by David J. Williams, American Chemical Society, 1983, Masao Kato and Hachiro Nakanishi, "Organic Nonlinear Optical Materials", C.M.C, 1985, and D. S. Chemla and J. Zyss, "Nonlinear Optical Properties of Organic Molecules and Crystals", vols. 1 and 2, Academic Press, 1987.

One of the applications of such a non-linear optical material is a wavelength conversion device using the second harmonic generation (SHG), the addition of frequencies (or sum frequency) and the subtraction of frequencies (or differential frequency) on the basis of a secondary non-linear effect. As such non-linear optical materials there have been put into practical use inorganic perovskites such as lithium niobate. However, $\pi$ electron-conjugated organic compounds containing electron donative groups and electron attractive groups have been known to far surpass the above mentioned inorganic substances in many non-linear optical properties.

In order to form a non-linear optical material with a higher performance, it is necessary to arrange a compound having a high non-linear susceptibility in molecular state in such a manner that no inverse symmetry occurs. It has been known that a compound having a long $\pi$ electron conjugate chain is useful for the development of a high non-linear susceptibility, which is one of the many non-linear optical properties. Various examples of such a compound are described in the above cited references. As can be seen by those skilled in the art, these compounds exhibit an absorption peak shifted in the long wavelength range. In particular, these compounds are subject to drop in the blue light transmittance which impedes the generation of blue light as second harmonic. This is true in the case of p-nitroaniline derivatives. The fact that the effficiency of the second harmonic generation greatly depends on the transmittance of the second harmonic can be proved by Alain Azema, "Proceedings of EPIE", vol. 400, Now Optical Materials, 1983, FIG. 4, page 186.

Thus, the apperance of a non-linear optical material which exhibits a high transmittance of blue light has been desired. It has been heretofore proposed to replace carbon atoms in benzene nucleus of nitroanline by nitrogen atoms or the like. However, this approach has not necessarily given satisfactory results.

On the other hand, better approaches have been disclosed in JP-A-62-210430 and JP-A-62-210432 (the term "JP-A" as used herein means an "unexamined published Japanese patent application").

Furthermore, many materials are disclosed in JP-A-62-59934, JP-A 63-23136, JP-A-63-26638, JP-B-63-31768 (the term "JP B" as used herein means an "examined Japanese patent publication"), JP-A-63-163827, JP-A 63-146025, JP-A-63-85526, JP A-63-239427, JP-A-1-100521, JP-A-64-56425, JP-A-1-102529, JP-A-1-102530, JP-A-1-237625, and JP-A-1-207724.

As previously mentioned, such a material should not only be satisfied in properties in molecular state but also essentially cause no inverse symmetry in molecular arrangement in aggregated state so that it can be effectively used as secondary non-linear optical material. However, it is extremely difficult in the art to expect such a molecular arrangement. Further, the probability of occurrence of such a molecular arrangement is not so high.

If such a material is used as device for the conversion of wavelength, it is necessary to thoroughly consider the molecular arrangement in the crystal. Many of the above mentioned materials are not necessarily considered thoroughly in this respect. Further, to date, no wavelength conversion devices using organic non-linear optical materials have ever appeared commercially.

The reason for this phenomenon can be thought as follows:

When the above mentioned non-linear optical material is used to form a fiber type light wavelength conversion device, the crystal is not oriented in such a direction that the maximum non-linear optical constant of the material can be utilized. After all, the light wavelength conversion device thus obtained doesn't exhibit so high a wavelength conversion efficiency.

Further, the longer the light wavelength conversion device is, the higher is the wavelength conversion efficiency attained thereby. However, the above mentioned material is difficult to form a homogeneous single crystal. Thus, such a material is also disadvantageous in that it is not suitable for the preparation of a long light wavelength conversion device.

SUMMARY OF THE INVENTION

It is therefore an object of the present invention to provide a novel compound and molecular crystal having a molecular arrangement suitable for the preparation of a wavelength conversion device excellent in the transmission of blue light and free of inverse symmetry.

It is another object of the present invention to provide a process utilizing responce for the conversion of light wavelength among non-linear responces.

It is further object of the present invention to provide a light wavelength conversion module which exhibits a high wavelength conversion efficiency and can easily produce a second harmonic in the blue light range.

These and other objects of the present invention will become more apparent from the following detailed description and examples.

These objects of the present invention are accomplished with a compound represented by formula:

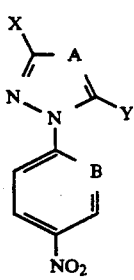

wherein X represents a methyl group or hydrogen atom, with the proviso that when X is a methyl group, A represents a nitrogen atom, Y represents a methyl group and B represents a nitrogen atom and when X is a hydrogen atom, A represents C—COOC$_2$H$_5$, Y represents a hydrogen atom and B represents C—CH$_3$.

In particular, the objects of the present invention are accomplished with a compound represented by formula (I), (II) or (III):

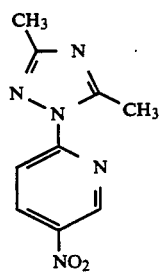

(I)

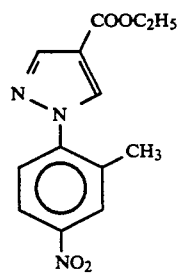

(II)

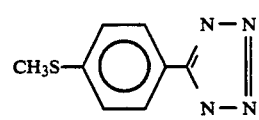

(III)

BRIEF DESCRIPTION OF THE DWAWINGS

By way of example and to make the description more clear, reference is made to the accompanying drawings in which:

FIG. 1 shows a powder process measuring equipment, and the numerals in the drawing are defined below:

1: powder sample, 2: fundamental wave cut filter, 3: spectrophotometer, 4: photomultiplier, 5: amplifier, (11): wavelength 1.064 μm, (12): wavelength 0.532 μm;

FIG. 3 shows the crystal structure of Compound (III) ((a): view projected in the direction of the axis a; (b): view projected in the direction of the axis b; (c): view projected in the direction of the axis c) (the axes a, b and c represent a vector.);

Figure 1:
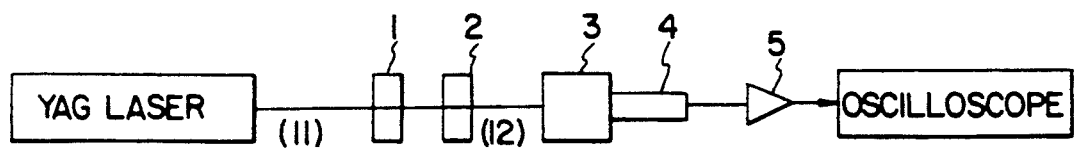

1: Nd: YAG laser, 2: fundamental wave (λ=1.064 μm), 2': second harmonic (λ=0.532 μm), 3: single crystal of Compound (I), 4: fundamental wave cut filter.

DETAILED ESCRIPTION OF THE INVENTION

The synthesis of compounds represented by formulae (I) and (II) (Compounds (I) and (II)) can be normally accomplished by the following method:

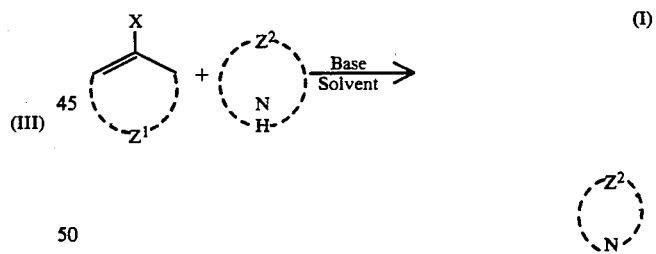

(I)

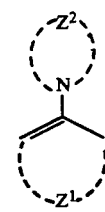

wherein X represents a halogen atom; Z$^1$ represents an atomic group required to form a benzene ring or pyridine ring; and Z$^2$ represents an atomic group required to form a triazole ring or pyrazole ring.

As the base to be used in this reaction there can be selected from organic bases such as pyridine, triethylamine and 1,8-diazabicyclo[5,4,0]-7-undecene, and inorganic bases such as potassium carbonate, sodium hydrogencarbonate, potassium-t-butoxide, hydrogenated sodium and sodium hydroxide. As solvent there can be used hydrocarbon such as n-hexane, ether such as tetrahydrofuran and 1,2-dimethoxyethane, amide such as N,N-dimethylformamide and N-methylpyrrolidone, sulfur-containing compound such as dimethyl sulfoxide and sulfolane, nitrile such as acetonitrile or ester such as ethyl acetate. Particularly preferred among these solvents are amide, sulfur-containing compound, and nitrile. The reaction may be effected at a temperature of −10° C. to 150° C., preferably 20° C. to 100° C.

The synthesis of a compound represented by formula (III) (compound (III)) can be normally accomplished by the following method. In particular, such a compound can be obtained by the reaction of 4-(methylthio)benzonitrile with sodium azide. As solvent there can be used an amide or the like. As catalyst there can be used an acid or base.

The reaction can be effected at a temperature of 50° to 150° C., preferably 80° to 120° C.

When the compound of the present invention is used as non-linear optical material, it may be used in any form such as powder, single crystal and material contained in host lattice (e.g., polymer, inclusion compound, solid solution, liquid crystal). The application of such a non-linear optical material is not limited to light wavelength conversion device. Such a non-linear optical material can be used as any device which utilizes a non-linear optical effect. Specific examples of devices other than light wavelength conversion device which can comprise the non-linear optical material of the present invention include optical bistable devices (e.g., optical memory device, optical pulse wavelength control device, optical limiter, differential amplifier device, optical transistor, A/D conversion device, optical logic device, optical multivibrator, optical flip-flop circuit), optical modulation device, and phase conjugate optical device.

Examples of method for the conversion of powder to single crystal include solution method such as solvent evaporation method, temperature drop method and vapor diffusion method, melting method such as Bridgman method, and sublimation method.

For the conversion of powder to single crystal, reference can be made to "Handbook of Crystallography", edited by Editorial Committee for Handbood of Crystallography, Kyoritsu Shuppan, 1971, 7th ed., Chapter 8.

In the conversion of wavelength, a single crystal having a proper size may be used. In this arrangement, the conversion of wavelength may be accomplished by angular phase matching or temperature phase matching method or Chelenkov radiation method using a waveguide path.

One embodiment of the arrangement using the latter method comprises a fiber type light wavelength conversion device and a light source. The arrangement of the present invention is characterized in that as the core of the light wavelength conversion device there is used a non-linear optical material represented by the general formula (I) and (III) in the form of single crystal, that the orientation of the crystal represented by the general formula (I) and (III) is such that the axis a extends substantially in the major axial direction of the core, and that the light source is adapted to direct to the light wavelength coversion device a fundamental wave linearly polarized to the axis b or c thereof perpendicular to the axis a.

Examples of laser light sources which emit such a fundamental wave are set forth in Table 1. The wavelength of the fundamental wave is not limited except for the effect of absorption by the above mentioned material. This is obvious from "Laser & Optronics", page 59, November 1987.

TABLE 1

| Name of laser | Oscillation wavelength and properties of various lasers | |
|---|---|---|
| | Oscillation wavelength (μm) 0.8 1.0 1.2 1.4 1.6 | Remarks (operation conditions: pulse CW, max. light output) |
| Semiconductor laser | | |
| GaInAsP/In laser | ⊢——⊣ (≈1.2–1.4) | CW Pmax = 200 mW (single mode) |
| GaAlAs/GaAs laser | ⊢⊣ (≈0.8) | CW Pmax = 150 mW (single mode) CW Pmax = 3 W (multiple mode) |
| InGaAs/GaAs laser | ⊢⊣ (≈1.0) | CW Pmax = 150 mW (single mode) CW Pmax = 3 W (multiple mode) |
| Solid laser | | |
| Nd:YAG laser | 0.946  1.064  1.32 | CW Pmax = 5 W (single mode) Q switch pulse Pmax = <10 MW |
| Ti:Al$_2$O$_3$ laser | ⊢———⊣ (≈0.8–1.0) | CW Pmax = 5 W (single mode) |
| Others | | |
| Dye laser | ⇐——⊣ | |

The present invention will be further described in the following examples, but the present invention should not be construed as being limited thereto.

EXAMPLE 1

Synthesis of Compound (I)

48.5 g (0.5 mol) of 3,5-dimethyl-1H-1,2,4-triazole, 79.3 g (0.5 mol) of 2-chloro-5-nitropyridine and 69.0 g (0.5 mol) of potassium carbonate were measured out and charged into a 500-ml three-necked flask equipped with an agitator and a thermometer. 250 ml of dimethyl sulfoxide (DMSO) was added to the reaction system. The reaction system was then stirred at a temperature of 50° C. for 5 hours. The reaction system was then allowed to cool to room temperature. The reaction system was then poured into 500 ml of ice-water. The resulting crystal was filtered off, and then washed with water. The crystal was recrystallized from acetone twice while being decolorized with activated carbon to obtain 48 g (yield: 43.8%) of Compound (I).

Melting point: 147° C.

$^1$H-nmr (δppm): 2.433 (3Hs), 2.914 (3Hs), 8.069 (1Hd), 8.617 (1Hdd), 9.316 (1Hd).

EXAMPLE 2

Synthesis of Compound (II)

1.40 g (10 mmol) of ethylpyrazole-4-carboxylate, 1.55 g (10 mmol) of 2-fluoro-5-nitrotoluene and 1.38 g (10 mmol) of potassium carbonate were measured out and charged into a 25-ml three-necked flask equipped with an agitator and a thermometer. 10 ml of DMSO was added to the reaction system. The reaction system was then stirred at a temperature of 50° C. for 5 hours. The reaction system was then allowed to cool to room temperature. The reaction system was then poured into 50 ml of ice-water. The resulting crystal was filtered off, and then washed with water. The crystal was recrystallized from ethanol twice while being decolorized with activated carbon to obtain 1.05 g (yield: 38.1%) of Compound (II).

Melting point: 105° C.

$^1$H-nmr (δppm): 1.385 (3Ht), 2.453 (3Hs), 4.359 (2Hq), 7.556 (1Hd), 8.161–8.256 (4H)

EXAMPLE 3

Synthesis of Compound (III)

3.0 g (0.02 mol) of 4-(methylthio)benzonitrile, 1.44 g (0.022 mol) of sodium azide and 0.12 g (0.0022 mol) of ammonium chloride were added to 20 ml of DMF. The reaction system was then stirred at a reaction temperature kept at 100° C. for 10 hours. After the completion of the reaction, water and concentrated hydrochloric acid were added to the reaction system so that it was acidified. The resulting crystal was filtered off, and then recrystallized from isopropyl alcohol to obtain 1.5 g (7.8 mml) of 5-(4-methylthiophenyl)-tetrazole (Compound (III)) (m.p. 222° C.).

Elementary analysis: Calculated % for $C_8H_8N_4S$: C49.98, H4.19, N29.14. Found %: C49.98, H4.12, N29.10.

EXAMPLE 4

For the evaluation of blue light transmission, various compounds in ethanol solution were measured for ultraviolet visible light absorption spectrum. The results are set forth in Table 2.

TABLE 2

| Compound | $\lambda_{max/nm}^{EtOH}$ | $\lambda_{c/nm}^{95}$ | $\lambda_{c/nm}^{99}$ | Remarks |
|---|---|---|---|---|
| 1 | 298 | 390 | 406 | Present Invention |
| 2 | 282 | 389 | 406 | " |
| DMNP | 311 | 402 | 414 | Comparative |
| DMNT | 285 | 390 | 408 | " |
| ENIM | 269 | 388 | 408 | " |

DMNP  DMNT  ENIM

TABLE 2-continued

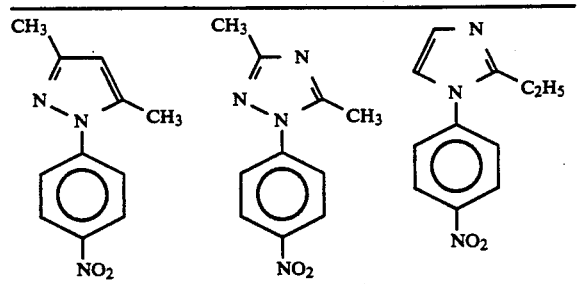

All these comparative compounds are disclosed in JP-A-62-210432.

In Table 2, $\lambda c^{95}$ and $\lambda c^{99}$ indicate the wavelength at which the compound shows a transmission of 95% and 99% in a $4 \times 10^{-4}$ mole/l ethanol solution, respectively.

The compound of the present invention exhibits a small skirt in the absorption curve and thus can be expected to exhibit an excellent blue light transmittance when used as crystal.

EXAMPLE 5

The compound of the present invention in the form of microcrystalline powder was measured for the generation of second harmonics in accordance with the method described in S. K. Kurtz and T. T. Perry, "Journal of Applied Physics", vol. 39, page 3798, 1968.

The measurement was effected by means of an apparatus shown in FIG. 1.

In the measurement, light from pulse YAG laser (λ=1.064 μm; beam diameter=approx. 1 mmφ; peak power=approx. 10 MW/cm$^2$) was used as fundamental wave. An evaluation apparatus shown in FIG. 1 was used to measure the second harmonic of the fundamental wave. The intensity of the second harmonic through each specimen was determined relative to that through urea. When the intensity of the second harmonic was weak, it was visually measured. In order to distinguish the second harmonic from light (mainly yellow and red) emitted by the absorption of two photons by the fundamental wave, a spectroscope was inserted in the system to measure the second harmonic alone. The main object of the powder process measurement is to see if the specimen has non-linearity. The ratio of the intensity of the second harmonic indicates the magnitude of the non-linearity.

The results are set forth in Table 3.

TABLE 3

| Compound | SHG (ratio to urea) | Remarks |
|---|---|---|
| (I) | 14 | Present Invention |
| (II) | 1 | " |
| A | 0 | Comparative Example |
| B | 0 | " |
| C | 0 | " |
| D | 0 | " |
| E | 0 | " |
| F | 0 | " |
| G | 0 | " |
| H | 0 | " |
| I | 0 | " |
| J | 0 | " |
| K | 0 | " |
| L | 0 | " |
| M | 0 | " |
| N | 0 | " |
| O | 0 | " |
| P | 0 | " |
| Q | 0 | " |

TABLE 3-continued

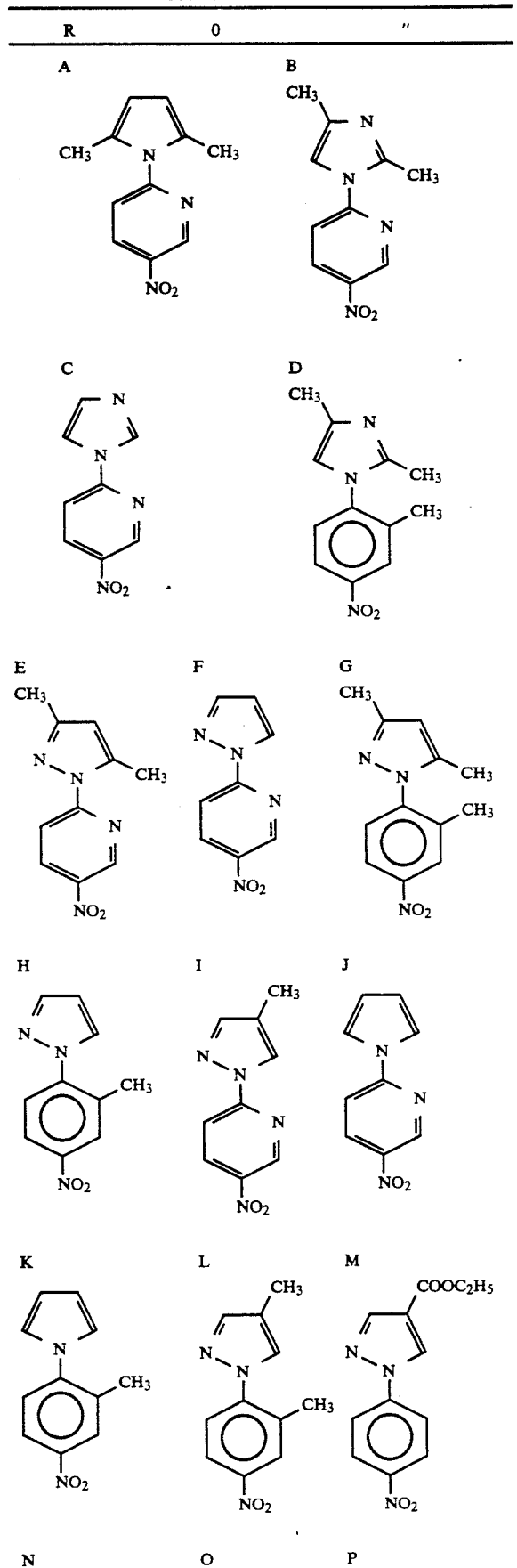
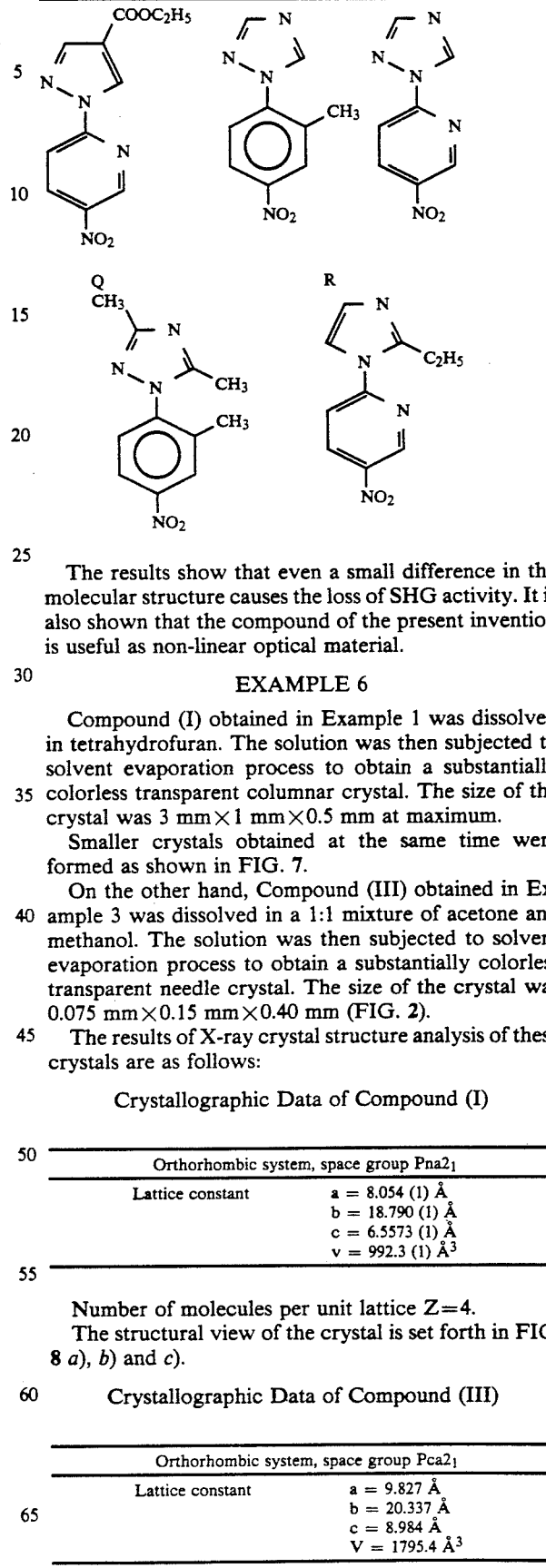

The results show that even a small difference in the molecular structure causes the loss of SHG activity. It is also shown that the compound of the present invention is useful as non-linear optical material.

EXAMPLE 6

Compound (I) obtained in Example 1 was dissolved in tetrahydrofuran. The solution was then subjected to solvent evaporation process to obtain a substantially colorless transparent columnar crystal. The size of the crystal was 3 mm×1 mm×0.5 mm at maximum.

Figure 7:
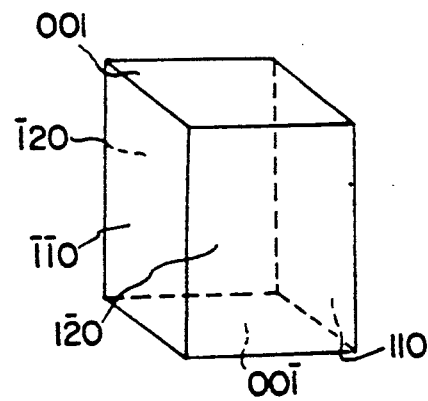
FIG. 7 shows the shape and face index of a substantially colorless transparent single crystal which extends in the direction of the axis c, prepared by solvent evaporation method from a tetrahydrofuran solution of Compound (I)

Smaller crystals obtained at the same time were formed as shown in FIG. 7.

Figure 2:
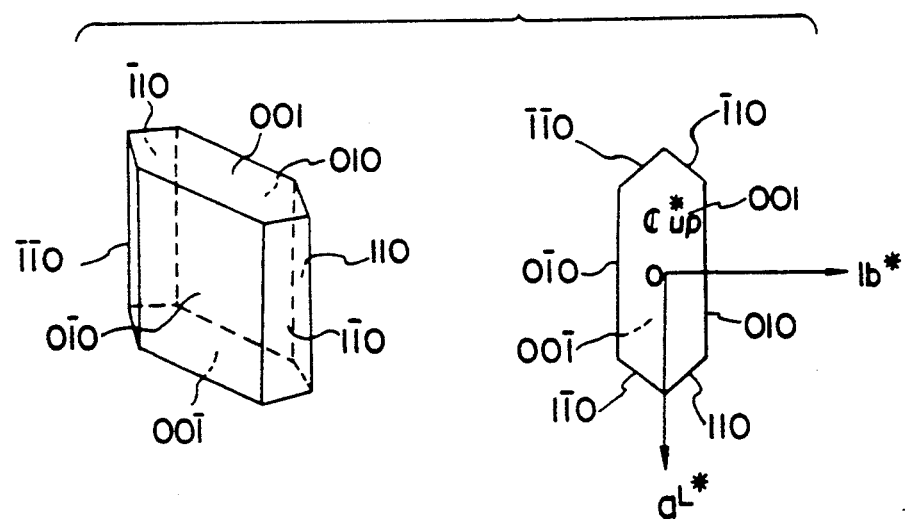
FIG. 2 shows the shape and face index of a colorless transparent single crystal which extends in the direction of the axis c (size: 0.075 mm×0.15 mm×0.40 mm) prepared by solvent evaporation method from a solution of Compound (III) in a 1:1 mixture of acetone and methanol.

On the other hand, Compound (III) obtained in Example 3 was dissolved in a 1:1 mixture of acetone and methanol. The solution was then subjected to solvent evaporation process to obtain a substantially colorless transparent needle crystal. The size of the crystal was 0.075 mm×0.15 mm×0.40 mm (FIG. 2).

The results of X-ray crystal structure analysis of these crystals are as follows:

Crystallographic Data of Compound (I)

| Orthorhombic system, space group Pna2$_1$ | |
|---|---|
| Lattice constant | a = 8.054 (1) Å |
| | b = 18.790 (1) Å |
| | c = 6.5573 (1) Å |
| | v = 992.3 (1) Å$^3$ |

Number of molecules per unit lattice Z=4.

Figure 8A:
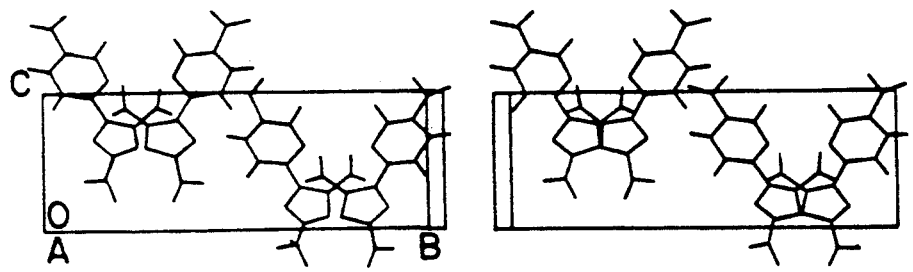
FIG. 8 shows the crystal structure of Compound (I) ((a): view sterically projected in the direction of the axis a; (b): view sterically projected in the direction of the axis b; (c): view sterically projected in the direction of the axis c)
Figure 8B:
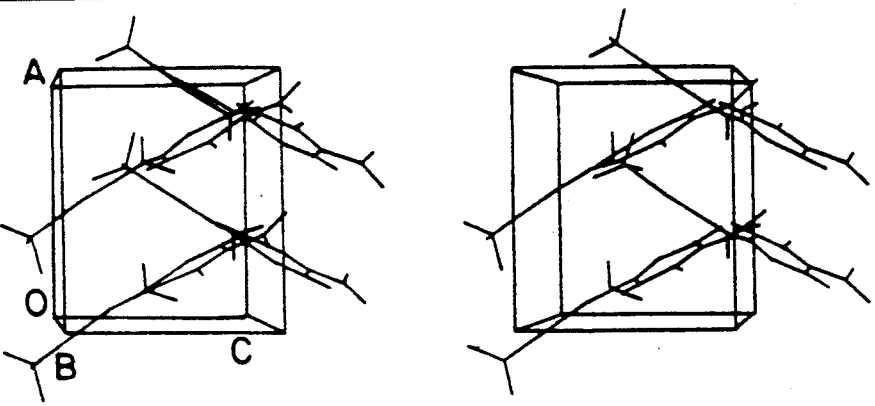
Figure 8C:
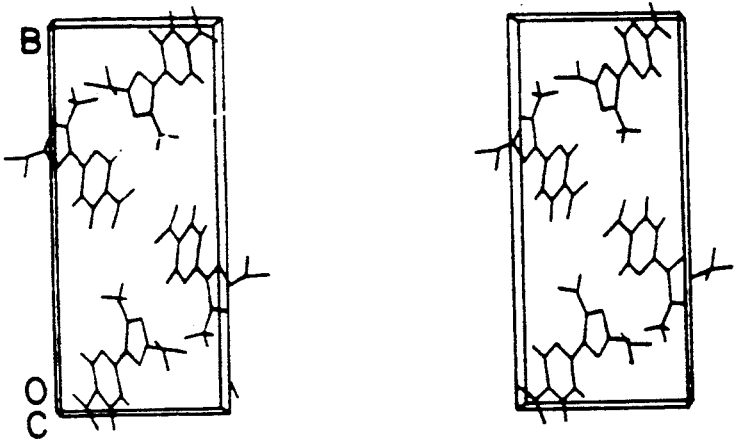

The structural view of the crystal is set forth in FIG. 8 a), b) and c).

Crystallographic Data of Compound (III)

| Orthorhombic system, space group Pca2$_1$ | |
|---|---|
| Lattice constant | a = 9.827 Å |
| | b = 20.337 Å |
| | c = 8.984 Å |
| | V = 1795.4 Å$^3$ |

Number of molecules per unit lattice Z=8.

The structural view of the crystal is set forth in FIG. 3 a), b) and c).

The space group in the above mentioned crystallographic data shows that the crystal has no inverse symmetry.

The maximum side length of Compound (III) in the form of single crystal is preferably 40 mm or more.

Figure 9:
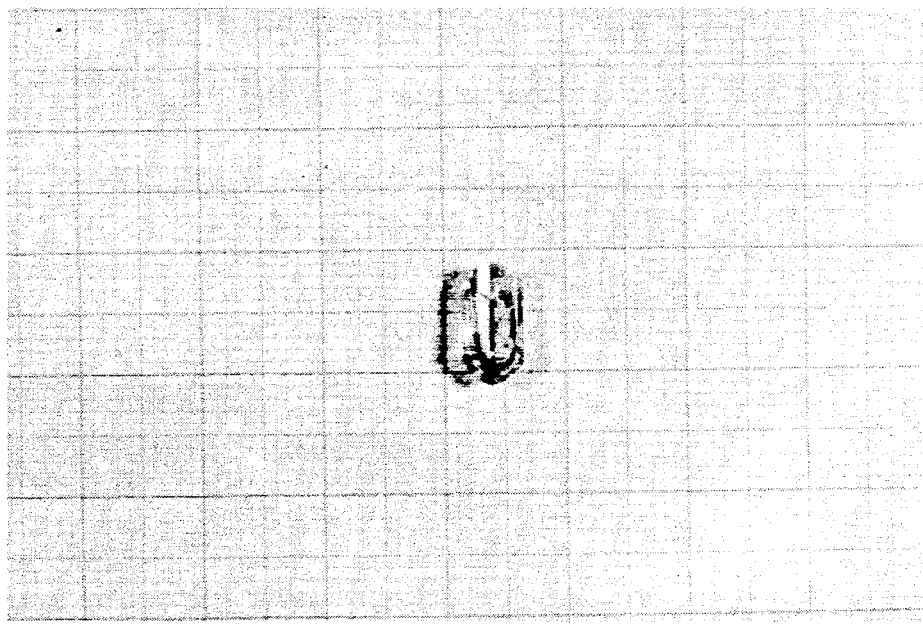
FIG. 9 shows the crystal structure of Compound (I) prepared by temperature drop method from an N,N-dimethyl formamide solution of the compound.

Compound (I) was obtained in the same crystalline form also by using acetone instead of tetrahydrofuran as solvent. Furthermore, Compound (I) was obtained in the form of crystal with a size of 10 mm×5 mm×3 mm (as shown in FIG. 9) by temperature drop process using N,N-dimethyl formamide.

The crystal thus obtained was identified as a single crystal by confirming the quenching position under a polarization microscope.

The maximum side length of the single crystal is preferably 1 mm or more.

EXAMPLE 7

The compound of the present invention in the form of microcrystalline powder was measured for the generation of second harmonics in accordance with the method described in S. K. Kurtz and T. T. Perry, "Journal of Applied Physics", vol. 39, page 3798, 1968.

The measurement was effected by means of an apparatus shown in FIG. 1.

In the measurement, light from pulse YAG laser ($\lambda=1.064$ μm; beam diameter=approx. 1 mmφ; peak power=approx 10 MW/cm$^2$) was used as fundamental wave. An evaluation apparatus shown in FIG. 1 was used to measure the second harmonic of the fundamental wave. The intensity of the second harmonic through each specimen was determined relative to that through urea. When the intensity of the second harmonic was weak, it was visually measured. In order to distinguish the second harmonic from light (mainly yellow and red) emitted by the absorption of two photons by the fundamental wave, a spectroscope was inserted in the system to measure the second harmonic alone. The main object of the powder process measurement is to see if the specimen has non-linearity. The ratio of the intensity of the second harmonic indicates the magnitude of the non-linearity.

The results are set forth in Table 4.

TABLE 4

| Compound (relation to the present invention) | SHG efficiency | $\lambda_{max/nm}^{EtOH}$ | $\lambda_{cut\ off}^{EtOH}$/nm |
| --- | --- | --- | --- |
| Compound (I) (present invention) | 1 | 298 | 390 |
| Compound (III) (present invention) | 1 | 285 | 329 |
| MNA (comparative) | 22 | 374 | 458 |
| NPRO (comparative) | 9.6 | 327 | 410 |
| DMNP (comparative) | 16 | 312 | 402 |
| BMC (comparative) | 10 | 321 | 411 |
| CMDT (comparative) | 0.1 | 368 | 403 |
| POM (comparative) | 16 | 324 | 408 |

In Table 4, $\lambda_{cut\ off}^{EtOH}$ indicates the wavelength at which the specimen exhibits a transmittance of 95% in a 4×10$^{-4}$ mol/l ethanol solution.

Table 4 shows that the compound of the present invention exhibits an excellent blue light transmittance.

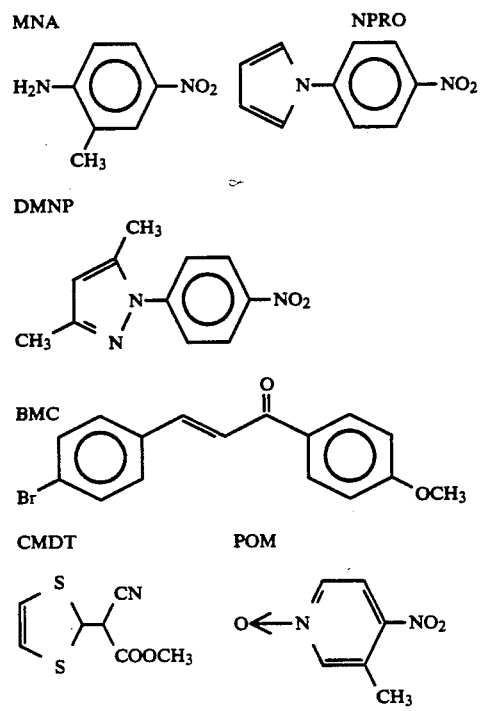

REFERENCE EXAMPLE 1

It has been known that the secondary non-linear optical constant ($\beta$) in the molecular state can be calculated on the basis of the calculation obtained by the molecular orbital method. This approach has been known as a useful method for molecular design. The value of $\beta$ calculated by PPP-CI method is set forth in Table 5.

TABLE 5

Calculation of $\beta$ ($\lambda = 1.064\mu$)

| Structure | Value |
| --- | --- |
| (present invention) | 22.45 × 10$^{-30}$ esu |
| (comparative) | 22.42 × 10$^{-30}$ esu |
| (comparative) | 22.18 × 10$^{-30}$ esu |

Table 3 shows that the compound of the present invention exhibits a great $\beta$ value and thus is a useful non-linear optical material, though its absorption end lies in the short wavelength range.

REFERENCE EXAMPLE 2

In the actual process for the formation of a fiber type light wavelength conversion device, it has been unknown how the crystal orientation should be predetermined and in which direction the direction of polarization of the fundamental wave to be incident thereon should be predetermined to provide a high wavelength conversion efficiency.

The process for the determination of the crystal orientation of non-linear optical material and the direction of linear polarization of fundamental wave suitable for high wavelength conversion efficiency will be described hereinafter.

The crystal of Compounds (I) and (III) are in orthorhombic system and belong to point group mm2. Therefore, the tensor of the non-linear optical constant is as follows:

$$d = \begin{pmatrix} 0 & 0 & 0 & 0 & d_{15} & 0 \\ 0 & 0 & 0 & d_{24} & 0 & 0 \\ d_{31} & d_{22} & d_{33} & 0 & 0 & 0 \end{pmatrix}$$

In this equation, assuming that the Optical axes X, Y and Z are defined with respect to the crystal axes a, b and c as shown in FIG. 3, $d_{31}$ is the non-linear optical constant in the case where light linearly polarized in the X direction (hereinafter referred to as "X polarization", same to Y and Z) is directed to the system as fundamental wave so that Z-polarized second harmonic is drawn. Similarly, $d_{32}$ is the non-linear optical constant in the case where Y-polarized fundamental wave is directed to the system so that Z-polarized second harmonic is drawn, $d_{33}$ is the non-linear optical constant in the case where Z-polarized fundamental wave is directed to the system so that Z-polarized second harmonic is drawn, $d_{24}$ is the non-linear optical constant in the case where Y- and Z-polarized fundamental wave is directed to the system so that Y-polarized second harmonic is drawn, and $d_{15}$ is the non-linear optical constant in the case where X- and Z-polarized fundamental wave is directed to the system so that X-polarized second harmonic is drawn. The magnitude of each non-linear optical constant will be described hereinafter.

Since the refractive index of Compounds (I) and (III) are not yet made clear, the value of $b_{IJK}$ from which the non-linear optical constant can be derived in the following equation is shown:

$$d_{IJK} = N \cdot f_I(2\omega) f_J(\omega) f_K(\omega) b_{IJK}$$

wherein N represents the number of molecules per unit volume; and $f(\omega)$ and $f(2\omega)$ represent local field modification factors for fundamental wave and second harmonic, respectively.

|          | Compound (I) | Compound (III) |
|----------|--------------|----------------|
| $b_{31}$ | 1.44         | 0.04           |
| $b_{32}$ | 2.08         | 8.51           |
| $b_{33}$ | 6.23         | 5.46           |
| $b_{15}$ | 1.44         | 0.04           |
| $b_{24}$ | 2.08         | 8.51           |

These $b_{IJK}$ values are based on X-ray crystal structural analysis and $\beta$ (unit: $\times 10^{-30}$ esu) which is calculated from PPP-CI MO method and Ward equation.

Figure 4:
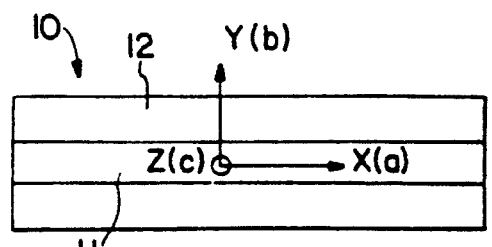
FIG. 4 shows a schematic view illustrating the crystal orientation of the core in the light wavelength conversion device according to the present invention.

The above table shows that $d_{32}$, $d_{33}$, $d_{24}$ and $d_{15}$ can take great values. Then, with the crystal (I) or (III) oriented in such an arrangement that its axis a (X axis in the optical system) extends in the direction of core axis (feasible by the method described later) as shown in FIG. 4 in the process for the formation of a fiber type light wavelength conversion device 10 by filling a clad 12 with a core 11 consisting of Compound (I) or (III), a fundamental wave linearly polarized in the direction of the axis b (Y axis in the optical system) or the axis c (Z axis in the optical system) can be directed to the light wavelength conversion device 10 to utilize the above mentioned great non-linear optical constants $d_{32}$ and $d_{33}$.

In order to utilize the non-linear optical constant $d_{24}$, Y- and Z-polarized wave needs to be input to a fiber type light wavelength conversion device. In order to utilize the non-linear optical constant $d_{15}$, X- and Z-polarized wave needs to be input to a fiber type light wavelength conversion device. Therefore, it is difficult to put the system in a single mode for higher conversion efficiency due to the refractive index anisotropy of Compound (I) or (III). On the contrary, in the case where Y-polarized or Z-polarized wave is input to the fiber type light wavelength conversion device, it is possible to sufficiently put the system in a single mode for higher conversion efficiency.

EXAMPLE 8

Figure 5:
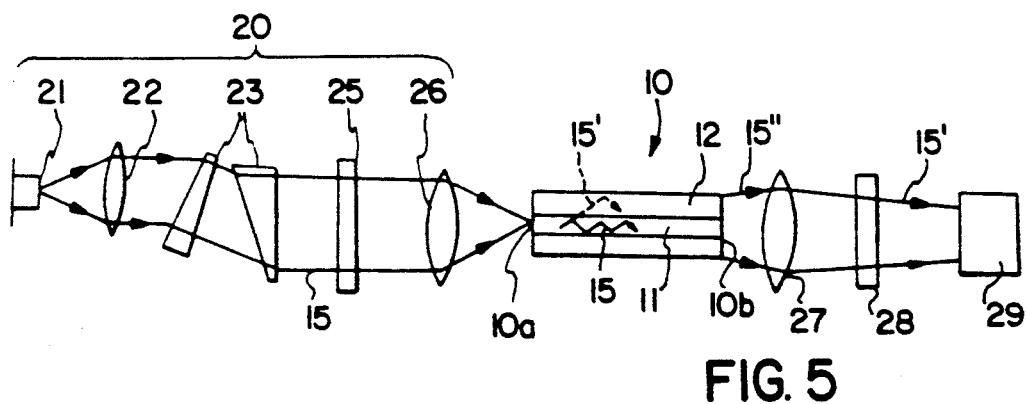
FIG. 5 shows a diagrammatic view illustrating the process for the preparation of the light wavelength conversion device according to the present invention.

FIG. 5 illustrates a light wavelength conversion module according to the 9th embodiment of the present invention. The light wavelength conversion module comprises a fiber type light wavelength conversion device 10, and a light source device 20 adapted to input a fundamental wave to the light wavelength conversion device 10.

A process for the preparation of the light wavelength conversion device 10 will be described hereinafter.

Figure 6:
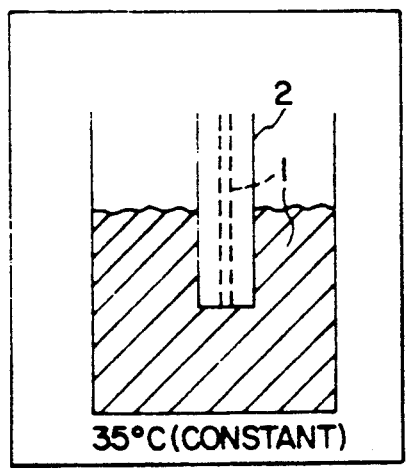
FIG. 6 shows a view of an apparatus for the growth of a single crystal using a fiber containing a single crystal of Compound (I) or (III) as core in solvent evaporation method.

Firstly, a hollow glass fiber is prepared as a clad. This glass fiber is made of, e.g., SFS3 glass fiber and has an outer diameter of about 100 μm and an inner diameter of 6 μm. On the other hand, Compound (I) is dissolved in 1 liter of acetone in an amount of 120 g, and Compound (III) is dissolved in 1 liter of a 1:1 mixture of acetone and methanol in an amount of 120 g. Thus, saturated solutions of Compounds (I) and (III) are prepared (at a temperature of 35° C.). One end of the glass fiber (clad) 2 is dipped in these saturated solutions 1 kept at a temperature of 35° C. in a constant temperature bath as shown in FIG. 6. These solutions then rise up through the glass fiber by capillary action. When the glass fiber is kept in this state, the mixture of acetone and methanol as solvent is evaporated to cause supersaturation. Then, crystal nuclei are formed in the hollow section of the glass fiber to cause single crystals to grow. As a result, a single crystal state with its crystal orientation uniformly arranged over a long range as 20 mm or more is obtained.

When the glass fiber 12 is filled with Compound (I) or (III) in the form of single crystal as mentioned above, the crystal orientation is such that the axis a (X axis in the optical system) extends in the direction of core axis as shown in FIG. 4.

After the core 11 is filled as mentioned above, the glass fiber 12 is cut at both ends thereof with a fiber cutter to form a light wavelength conversion device 10 having a length of 10 mm. As shown in FIG. 5, the light wavelength conversion device 10 is combined with a light source device 20 to form a light wavelength conversion module. In the present example, a semiconductor laser 21 is used as a light source which emitts a fundamental wave. Laser light (fundamental wave) with a wavelength of 820 mm emitted from the semiconductor laser 21 is then collimated through a collimator lens 22. The collimated beam is then passed through an anamorphic prism pair 23 and a λ/2 plate 25. The beam is converged through a condenser 26 into a small beam spot which is then incident on an entrance end surface 10a of the light wavelength conversion device 10. Then, the fundamental wave 15 is input to the light wavelength conversion device 10. As mentioned above, the crystal of Compound (I) or (III), which constitutes the core 11, is oriented such that X axis extends in the direction of core axis. In this example, the λ/2 plate in the light source device is rotated so that Y-polarized fundamental wave 15 is input to the light wavelength conversion device 10.

The fundamental wave 15 which is incident upon the light wavelength conversion device 10 is converted to a second harmonic 15' having half the fundamental wavelength (=410 nm) by Compound (I) or (III), which constitutes the core 11. The second harmonic 15' travels in the device 10 while repeating total reflection by the outer surface of the clad 12. The phase matching is effected between the mode of the fundamental wave 15 guided by the core 11 and the mode of the second harmonic 15' radiated to the clad 12 (so-called Chelenkov radiation).

The emission end surface 10b of the light wavelength conversion device 10 emitts a beam 15" comprising a mixture of the second harmonic 15' and the fundamental 15. The beam 15" thus emitted is condensed through a condensing lens 27. The beam 15" is then filtered through a band pass filter 28 (which satisfactorily transmits the second harmonic 15' having a wavelength of 410 nm but absorbs the fundamental wave 15 of 820 nm) so that only the second harmonic 15' having a wavelength of 410 nm is withdrawn. The second harmonic 15' was confirmed by a polarizing plate to be Z-polarized. In other words, the non-linear optical constant $d_{32}$ of Compound (I) or (III) is employed in this example. The second harmonic 15' was measured by a light power meter 29 for light intensity to determine the light wavelength conversion efficiency. The result was about 1% as calculated in terms of 1 W.

EXAMPLE 9

Figure 10:
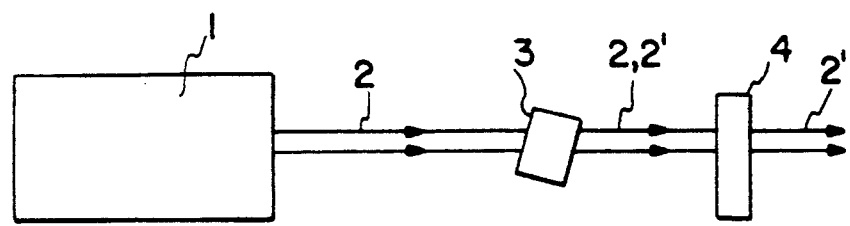
FIG. 10 shows a schematic view of a second harmonic generating apparatus using the crystal of FIG. 9, and the numerals in the drawing are defined below.

The generation of a second harmonic was effected by means of a single crystal as shown in FIG. 9. Specifically, the experiment was conducted by means of an apparatus as shown in FIG. 10. As a result, it was possible to observe a beam of green light with a wavelength of 532 nm. This indicates the possibility of phase matching. This shows that the crystal of the present invention is useful as non-linear optical material for the conversion of light wavelength.

REFERENCE EXAMPLE 3

In order to confirm blue light transmittance, the absorption spetrum of these specimens were measured. The results are set forth in Table 2. Table 2 shows that the compound of the present invention exhibits an excellent blue light transmittance.

As mentioned in the foregoing description, the molecular crystal constituted by molecules represented by the general formula (I), (II) or (III) of the present invention exhibits a high blue light transmittance and has no inverse symmetry in its molecular arrangement. Therefore, the molecular crystal of the present invention exhibits a secondary non-linear optical effect. Thus, the molecular crystal of the present invention is a useful material for the conversion of wavelength using a secondary non-linear optical effect. The molecular crystal of the present invention is particularly useful for the generation of a wave converted in the blue light range. As mentioned in detail in the foregoing description, in the light wavelength conversion module of the present invention, a high non-linear optical constant possessed by Compound (I) or (III) can be actually employed in a fiber type non-linear optical material. Furthermore, with such an arrangement, a light wavelength conversion device having a sufficient length can be formed. Thus, an extremely high wavelength conversion efficiency can be realized. Since Compound (I) or (III) exhibits an absorption end in the vicinity of 400 nm, the light wavelength conversion module enables an efficient generation of a second harmonic in the blue light range from laser light with a wavelength of about 800 nm as fundamental wave.

While the present system has been described with reference to Chelenkov radiation process, the present invention is not limited thereto. The present system also enables phase matching between guided waves. The conversion of wavelength is not limited to second harmonic. The present system can also be used for the generation of third harmonic, the generation of the addition of frequencies (or sum frequency), the generation of the subtraction of frequencies (or differential frequency), etc.

A second harmonic can also be generated by inputting YAG laser light to a bulk crystal cut from a single crystal of these compounds. The phase matching in this process is carried out by angular phase matching. Such a bulk single crystal can be used not only outside the cavity in the laser but also inside the cavity in a solid laser such as LD-excited solid laser to provide a higher wavelength conversion efficiency. The wavelength conversion efficiency can also be improved by installing the bulk single crystal in the resonator in an external resonator type LD.

When these compounds are converted to single crystal, Bridgman method, solvent evaporation method, etc can be employed.

This wavelength conversion system is not limited to second harmonic and can also be used for the generation of third harmonic, the addition of frequencies (or sum frequency), the substraction of frequencies (differential frequency), etc.

While the invention has been described in detail and with reference to specific embodiments thereof, it will be apparent to one skilled in the art that various changes and modifications can be made therein without departing from the spirit and scope thereof.

What is claimed is:

1. A non-linear optical material represented by the formula (II):

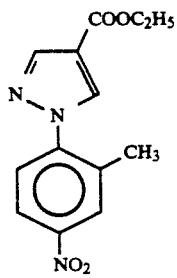
(II)
2. An orthorhombic molecular crystal having a space group of Pna2₁, constituted by molecules represented by formula (I):
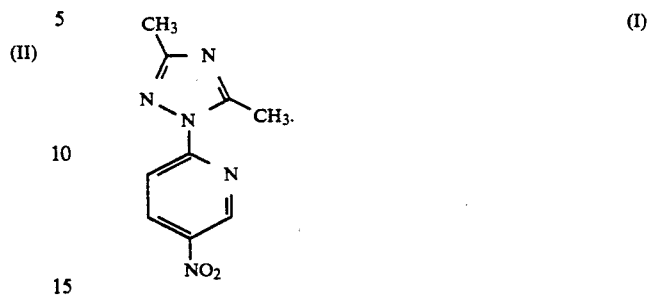
* * * * *